(12) United States Patent
Hsieh et al.

(10) Patent No.: US 7,141,430 B2
(45) Date of Patent: Nov. 28, 2006

(54) MICRORESPIROMETER AND ASSOCIATED METHODS

(76) Inventors: Yuch Ping Hsieh, 2121 Springwood Dr., Auburn, AL (US) 36830; Yun-Hwa Peggy Hsieh, 2121 Springwood Dr., Auburn, AL (US) 36830

( * ) Notice: Subject to any disclaimer, the term of this patent is extended or adjusted under 35 U.S.C. 154(b) by 455 days.

(21) Appl. No.: 09/990,783

(22) Filed: Nov. 14, 2001

(65) Prior Publication Data

US 2002/0061596 A1    May 23, 2002

Related U.S. Application Data

(60) Provisional application No. 60/249,771, filed on Nov. 17, 2000.

(51) Int. Cl.
*G01N 33/00* (2006.01)
*G01N 35/02* (2006.01)
*G01N 31/16* (2006.01)

(52) U.S. Cl. .......................... 436/133; 436/34; 436/51; 436/163

(58) Field of Classification Search ................ 436/20, 436/25, 34, 51, 163, 167, 168, 133, 145, 436/146, 181, 175, 174, 155, 160
See application file for complete search history.

(56) References Cited

U.S. PATENT DOCUMENTS

| | | | | |
|---|---|---|---|---|
| 3,865,548 A | * | 2/1975 | Padawer | 436/165 |
| 4,068,005 A | * | 1/1978 | Chicoye et al. | 426/16 |
| 4,994,117 A | * | 2/1991 | Fehder | 436/133 |
| 6,368,870 B1 | * | 4/2002 | Harp | 436/177 |

OTHER PUBLICATIONS

Trach "Shaking Soda Cans", http://www.newton.dep.anl.gov/askasci/chem03/chem03164.htm.*
Baker et al. "Equilibrium Vapor Method to Determine the Concentration of Inorganic Carbon And Other Compounds in Water Samples" http://toxics.usgs.gov/pubs/wri99-4018/Volume3/SectionA/3205_Baker/ Mar. 8-12, 1999.*
Rowell "Colorimetric method for CO2 measurement in soil", Soil Biol. Biochem., 1995, v. 27, No. 3, pp. 373-375.*
Grogan "CO2 flux measurement using soda lime: correction for water formed during CO2 adsorption" http://www.findarticles.com/p/articles/mi_m2120/is_n4_v79/ai_20793944, Jun. 1998.*
Stotzky "Microbial Respiration", Method of Soil Analysis, Part 2, 1965, pp. 1550-1572.*
Rowell "Colorimetric method for CO2 measurement in soils", Soil Biol. Biochem., 1995, v. 27, No. 3, pp. 373-375.*

* cited by examiner

*Primary Examiner*—Yelena G. Gakh
(74) *Attorney, Agent, or Firm*—Allen, Dyer, Doppelt, Milbrath & Gilchrist, P.A.

(57) ABSTRACT

A method for measuring an evolution rate of a gas from a sample includes equilibrating a sample with an alkaline solution and a pH indicator and permitting the alkaline solution to absorb formed carbon dioxide in an enclosed headspace. From the pH indicator at equilibrium is determined a time increment at which an increment of the alkaline solution is consumed by the $CO_2$. Carbon dioxide evolution rate is calculated from the time increment, the volume increment, and the alkaline solution concentration. A device for performing this measurement includes a sample vial and a reaction chamber having an opening adapted for mating with a sample vial opening and an opening for receiving the solution. The reaction chamber is dimensioned for equilibrating the sample with the alkaline solution and for determining the time increment required for an increment of the alkaline solution to be consumed by $CO_2$.

12 Claims, 3 Drawing Sheets

MICRORESPIROMETER AND ASSOCIATED METHODS

CROSS-REFERENCE TO RELATED APPLICATION

This application claims priority from commonly owned provisional application Ser. No. 60/249,771, filed Nov. 17, 2000, "Carbon Dioxide Microrespirometer."

BACKGROUND OF THE INVENTION

1. Field of the Invention

The present invention relates to a device and method for determining gas evolution rates in solids and liquids, and, more particularly, to such a device and method for determining carbon dioxide evolution rates in a sample.

2. Description of Related Art

Respiration is a common indicator of biological activity. Respirometry, the measurement of respiration rates, has been applied to a broad spectrum of applied and environmental microbiology, such as toxicity, with treatability, process control, and prediction of biological oxygen demand ($BOD_5$) in wastewater treatment, assessment of metal toxicity, living soil microbial biomass, and food quality.

Respiration rates can be measured either by rates of oxygen consumption or $CO_2$ evolution. Rapid oxygen consumption rate can be measured by using an oxygen probe or a quantitative electrolytic cell. Most oxygen respirometers, however, are applicable only to liquid samples. Oxygen respirometers with an electrolytic cell can be used to determine respiration of solid or semisolid samples, but their sensitivity is compromised.

Sensitive and rapid $CO_2$ respirometers based on infrared (ir) detectors have been developed in the past three decades and can handle solid samples with high speed and sensitivity. Instrumental respirometers are technically complicated and expensive if accuracy and sensitivity are needed. Noninstrumental $CO_2$ respirometers operated by an alkaline trap and acid-base titration have been in existence for many years. They are simple but relatively slow, with a measurement time in days, and less sensitive, with a detection limit in mL $CO_2$/day. Sensitive and rapid determination of respiration rates is highly desirable in monitoring microbial activity in food and environmental samples. A desired sensitivity, for example, would comprise one in the microliter $CO_2$ per hour level, and a rapidity of determination within about an hour.

SUMMARY OF THE INVENTION

It is therefore an object of the present invention to provide a device and method for determining gas evolution rates rapidly and sensitively.

It is another object to provide such a device and method for determining $CO_2$ evolution rates directly.

It is an additional object to provide such a device and method for use with solid or liquid samples.

It is a further object to provide such a device and method having a modest cost.

It is also an object to provide such a device and method operable under laboratory or remote site conditions.

These and other objects are attained by the present invention, a first aspect of which is a method for measuring an evolution rate of a gas from a sample. The method comprises the steps of pre-incubating a sample in gas communication with a solution comprising an alkaline solution and a pH indicator and permitting the alkaline solution to absorb formed carbon dioxide in an enclosed headspace. After the $CO_2$ absorption/evolution equilibrium is attained, from a change in the pH indicator is determined a time increment at which a small increment of the alkaline solution is substantially consumed by the $CO_2$ evolved. A calculation is made of a carbon dioxide evolution rate from the time increment, the small increment volume and concentration of the alkaline solution.

Another aspect of the invention is a device for measuring an evolution rate of a gas from a sample. The device comprises a sample vial having an opening into an interior space for containing a sample therein. The device further comprises a reaction chamber having an opening adapted for mating with the sample vial opening and a solution-receiving opening for receiving a solution comprising an alkaline solution and a pH indicator. The reaction chamber is dimensioned for receiving a predetermined amount of the alkaline solution to absorb formed $CO_2$ from a sample within the headspace.

A further aspect of the invention is a system for measuring an evolution rate of a gas from a sample. The system comprises a respirometer device as described above and means for determining from a change in color in the pH indicator a time increment at which a small increment of the alkaline solution is substantially consumed by the $CO_2$ from the sample.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
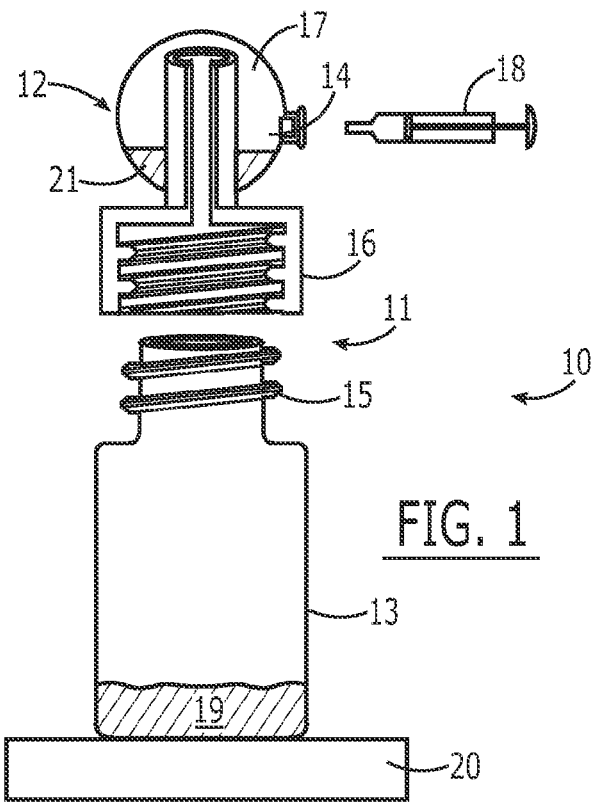
FIG. 1 is a schematic illustration of a microrespirometer of the present invention.
Figure 2:
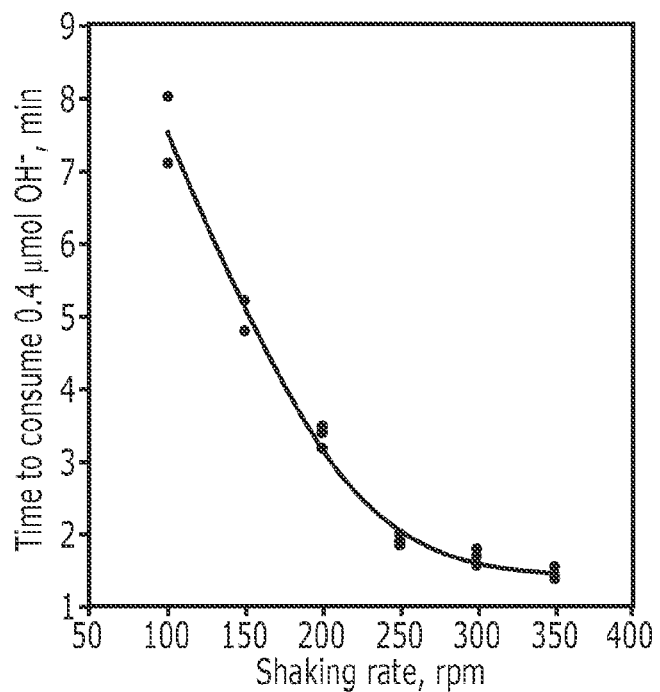
FIG. 2 is a graph of $CO_2$ absorption versus shaking rate of the microrespirometer.

A description of the preferred embodiments of the present invention will now be presented with reference to FIGS. 1–6.

The basis of the system 10 and method of the present invention is to establish a carbon dioxide absorption/evolution steady state between an alkaline solution and a sample. After the steady state is attained, an indicator comprising, for example, phenolphthalein, is used to indicate the end point of a small increment of the alkaline solution being consumed by the $CO_2$ evolved.

The system 10 of the present invention comprises a microrespirometer device 11 (FIG. 1), which in turn comprises a substantially transparent reaction chamber 12 and sample vial 13. The reaction chamber 12 comprises a small alkaline trap with a total headspace of 6–7 mL having a small septum hole 14. The sample vial 13 size is variable, and exemplary sizes include 25, 30, 40, and 75 mL (e.g., Fisherbrand EPA bottles, Suwanee, Ga.). The reaction chamber 12 and sample vial 13 are coupled through a standard threaded screw 15 and septum liner 16 to form a closed headspace 17.

An alkaline solution 21 is injectable, such as using a syringe 18, into the reaction chamber 12 via a solution-receiving opening 18, and a sample 19 is placeable in the sample vial 13. The alkaline solution absorbs the $CO_2$ in the headspace 17. The indicator in the alkaline solution changes color when the alkaline solution is "consumed" by $CO_2$. Preferably the microrespirometer 11 is shaken at a fixed rate (e.g., 240 rpm) on an orbital shaker 20 to enhance $CO_2$ absorption.

The alkaline solution of the present invention comprises a solution of NaOH, $BaCl_2$, and indicator, with an equal molar ratio of NaOH and $BaCl_2$ and 0.5 mL indicator solution, with 0.5% phenolphthalein in 50% ethanol solution, per 50 mL alkaline solution. $BaCl_2$ in the alkaline solution precipitates the absorbed $CO_2$, which ensures the stoichiometry of 2 moles of alkaline spent per mole of $CO_2$ absorbed:

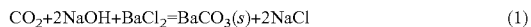

$$CO_2 + 2NaOH + BaCl_2 = BaCO_3(s) + 2NaCl \quad (1)$$

$BaCl_2$ also sharpens the change of color at the end point when a very low level of respiration is being determined. The alkaline solution is stored in a septum-capped vial to prevent absorption of $CO_2$ from the air. The alkaline solution is transferred through, for example, a syringe 18.

Optimal operating conditions for the system 10 were determined with a series of experiments. The effect of shaking on the $CO_2$ absorption of the microrespirometer 11 was investigated by coupling microrespirometers 11 with empty 25-mL sample vials 13 in a glove box having a known $CO_2$ concentration, as determined with an ir $CO_2$ analyzer.

A 0.2-mL portion of 0.002M alkaline solution was injected into each reaction chamber 12. The microrespirometers 11 were shaken at fixed rates of 100, 150, 200, 250, and 300 rpm. The time required to consume the alkaline solution in each microrespirometer 11, as indicated by the indicator color change, was recorded. Each test was repeated in triplicate, and the results are plotted in FIG. 2. The $CO_2$ absorption is shown to increase as the shaking rate is increased from 100 to 250 rpm. The increase in $CO_2$ absorption levels off when the shaking rate exceeded 250 rpm. Shaking at 200 rpm or higher improves reproducibility of $CO_2$ absorption. A fixed shaking rate between 200 and 250 rpm is recommended for the microrespirometer 11 because the benefit of shaking is achieved while the difficulty of operation at higher rates is avoided.

The effect of alkaline concentration on the absorption of $CO_2$ in a closed headspace 17 was investigated at 25° C. A 25-mL sample vial was connected to an ir analyzer so that the vial 13 and ir detector formed a closed headspace 17 in which air circulated continuously. The 25-mL vial 13 was shaken at 240 rmp on an orbital shaker 20. 1-mL portions of 0.2, 0.1, 0.01, and 0.0011M were injected into the vial 13 through the solution-receiving opening 18 at the beginning of the experiment, and the concentration of $CO_2$ in the vial 13 was recorded periodically.

Figure 3:
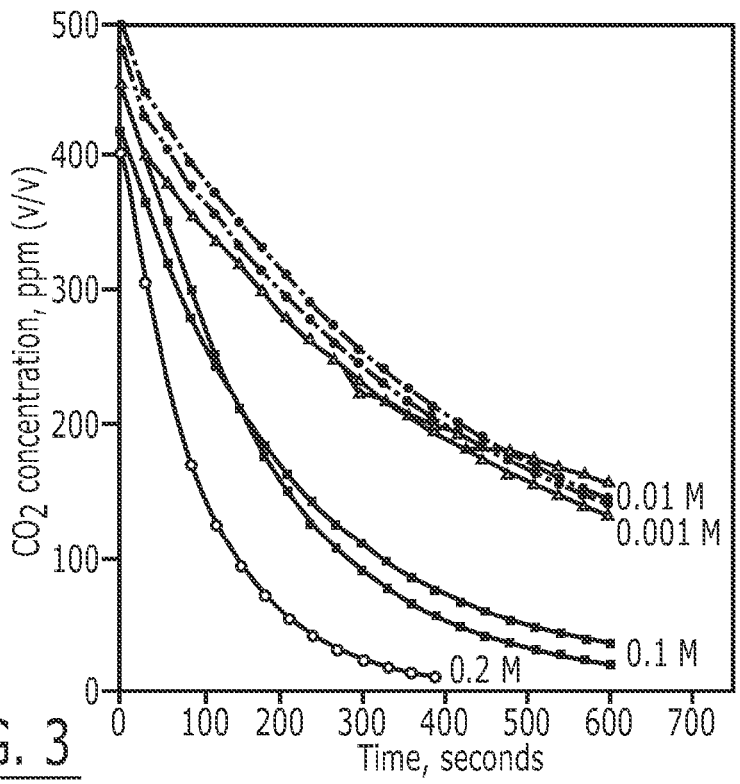
FIG. 3 is a graph of $CO_2$ absorption and concentration of an alkaline solution in the microrespirometer.

The experiment was repeated twice, and the results are plotted in FIG. 3, where each dot represents a single measurement. It can be seen that as the concentration of alkaline solution decreases from 0.2 to 0.01M, the $CO_2$ absorption rate decreases as well. The $CO_2$ absorption rate does not decrease further as the alkaline concentration is reduced from 0.01 to 0.001M. It is not believed possible to have complete absorption of CO2 in the headspace 17 of the microrespirometer 11 in a matter of hours when the concentration of the alkaline solution is less than 0.01M. The concentration of the alkaline solution has to be much less than 0.01M in order to determine $CO_2$ evolution rate at a microliter per hour level. The microrespirometer 11 therefore does not work on the principle of complete $CO_2$ absorption, but on an absorption/evolution steady state principle that will be discussed in the following.

An alkaline solution of less than 0.0005M is not sufficiently stable to be used in the microrespirometer 11 because the possibility of contamination from ambient $CO_2$ is too large for such low alkalinity. Phenolphthalein is not stable in alkaline concentrations exceeding 0.01M; the deep pink color fades away by itself within 1 h. Therefore, a preferred alkaline concentration range suitable for the microrespirometer 11 is between 0.01 and 0.001M.

The relationship between $CO_2$ absorption rate and the $CO_2$ concentration in the headspace 17 of the microrespirometer 11 was also investigated. Microrespirometers 11 with a 75-mL sample vial 13 were coupled in a glove box of known $CO_2$ concentration. Increments of 0.1 mL 0.002M alkaline solution were injected into the reaction chamber 12. The microrespirometers 11 were shaken at 240 rpm, and the time required to consume each increment of the alkaline solution was recorded. The consumption of each increment of the alkaline solution, for example, 0.2 μmol alkaline, or 0.1 μmol $CO_2$, represents a 29.7-ppm (v/v) reduction of $CO_2$ concentration in the 82-mL microrespirometer 11 at 25° C. Each treatment was performed in triplicate, and the results are plotted in FIG. 4, with each dot representing a single measurement.

In using the microrespirometer 11 of the present invention, a portion of solid or liquid sample 19 is placed in the sample vial 13, and the vial 13 is coupled to the reaction chamber 12. 0.8 mL alkaline solution of a desired concentration is injected into the reaction chamber 12 using a syringe 18. The respirometer 11 is shaken at a fixed rate, for example, 240 rpm, for 30 min, which comprises the pre-incubation, pre-steady-state period, ensuring that the alkaline solution is not completely consumed during this time. If the alkaline solution is about to be consumed, more alkaline solution is injected into the reaction chamber 12. After the 30-min pre-incubation, pre-steady-state period the shaker 20 is stopped, and the alkaline solution in the chamber 12 is withdrawn to leave 0.1–0.2 mL. The respirometer 11 is continued to be shaken until the alkaline solution changes to a faint pink color. The shaker 20 is stopped immediately, and 0.1 mL alkaline solution is injected, shaking is resumed, and the time required to consume the alkalinity is recorded.

In an alternate embodiment, all the alkaline solution in the chamber 12 is withdrawn, and a new 0.1 mL portion of alkaline solution is injected prior to resuming the shaking.

In either case, once the first indicator change has been recorded, increments of 0.1 mL alkaline solution are injected a predetermined number of further times, for example, twice more, and the time required to consume each increment is recorded.

The average of the times required to consume each 0.1-mL increment is used to calculate $CO_2$ evolution rate using the following formula:

$$\text{carbon dioxide evolution rate } (\mu mol/h) = (V \times 10^3 \times M/2)/(t/60)$$

where M is the molarity of the alkaline concentration of the solution, V is a volume of the increment of the alkaline solution in millileters, and t is the time increment in minutes. microliters per hour by multiplying the molar volume of $CO_2$ at a specific temperature.

Figure 4:
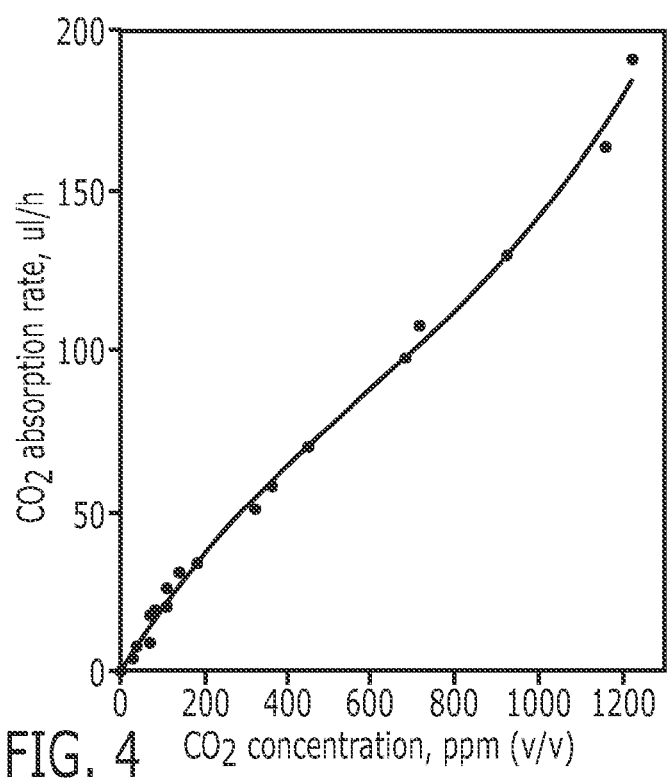
FIG. 4 is a graph of $CO_2$ absorption rate versus $CO_2$ concentration in the headspace of the microrespirometer.

The relationships between the $CO_2$ absorption rate of a 0.002M alkaline solution and the concentration of the $CO_2$ in the headspace 17 is shown in FIG. 4. In general, the $CO_2$ absorption rate has a positive curve-linear relationship with the concentration of $CO_2$. The $CO_2$ absorption rate of the respirometer 11 at a given temperature and shaking rate reflects the $CO_2$ concentration in the headspace 17, which may not be the $CO_2$ evolution rate of the sample. However, if a sample is equilibrated with the alkaline solution in the respirometer at a given temperature and shaking rate, the concentration of $CO_2$ in the respirometer would eventually reach a constant value when the $CO_2$ absorption rate equals the $CO_2$ evolution rate. For example, if the starting $CO_2$ evolution rate of the sample 19 is 100 $\mu$L/h, the $CO_2$ concentration of the respirometer 11 is increased to about 660 ppm and remain there because an steady state of $CO_2$ absorption and evolution is established. If the $CO_2$ evolution rate of the sample is 20 $\mu$L/h, the $CO_2$ concentration of the respirometer 11 is decreased to about 150 ppm, where an absorption/evolution steady state is established. The $CO_2$ evolution rate of a sample 19, therefore, can be determined by the $CO_2$ absorption rate of the microrespirometer 11 when a steady state established. That is, after a sample reaches is steady state with an alkaline solution in a microrespirometer 11 of the present invention, the $CO_2$ evolution rate can be determined by the time required to consume a small increment of the alkaline solution, as shown in Eq. (2).

The minimum time required for a sample 19 in the respirometer 11 to reach steady state is deduced from a computer simulation based on a relationship between the $CO_2$ absorption rate and the $CO_2$ concentration of the respirometer 11 and the $CO_2$ evolution rate of the sample 19. That is, the concentration of $CO_2$ in the headspace 17 after being shaken for a small increment of time $\Delta t$ is $$C_{i+\Delta t} = C_i + (E - A_{Ci}) \Delta t / V_{headspace} \quad (3)$$

where $C_i$ and $C_{i+\Delta t}$ are the $CO_2$ concentrations of the respirometer at time i and time i+$\Delta t$, respectively. $A_{Ci}$ is the $CO_2$ absorption rate of the respirometer at time i and is a function of the $CO_2$ concentration $C_i$. E is the $CO_2$ evolution rate of the sample 19, and $V_{headspace}$ is the volume of the headspace 17.

The mathematical relationship of $A_{Ci}$ and $C_i$ was generated by a nonlinear regression curve fitting program (Table Curve, Jandel Scientific, San Rafael, Calif.) using the data of FIG. 4. The regression enabled the calculation of $A_{Ci}$ based on $C_i$. The values of $A_{Ci}$, $C_i$, and $C_{i+\Delta t}$ for each small time increment (0.5 min) of $\Delta t$ were calculated and tabulated using a spreadsheet software (Excel, Microsoft, Redmond, Wash.) based on Eq. (3). Steady state is attained in the simulation when the $CO_2$ concentration in the respirometer approaches a constant, i.e., (E–$A_{Ci}$) approaches 0 and $C_{i+\Delta t}$ approaches $C_i$. The minimum time required to attain an steady state is the sum of all small time increments, $\Delta t$, during which $CO_2$ concentration approaches a constant. The headspace $CO_2$ concentration, expressed as as a percentage of the final steady-state headspace $CO_2$ concentration versus time of pre-incubation is presented in FIG. 5 for a range of respiration rates. Two headspace volumes of the respirometer, i.e., 12 mL (5 mL remaining headspace in the sample vial plus 7 mL in the reaction chamber) and 27 mL (20 mL remaining headspace in the sample vial plus 7 mL in the reaction chamber) were simulated in FIG. 5.

The results indicate that the smaller the headspace 17, the quicker steady-state is reached, and that the greater the $CO_2$ evolution rates, the quicker an steady state is reached. For example, in the 12-mL headspace case, a 30 min preincubation, pre-steady-state period is sufficient for the measurement of all $CO_2$ evolution rates $\geqq 1$ $\mu$L/h. In the 27 mL headspace case, 100–107% of equilibrated value can be attained within 45 min for all $CO_2$ evolution rates, except the 1 $\mu$L/h case. The working range of the respirometer is designed to be 1–300 $\mu$L/h, which requires 30–45 min of pre-incubation time, according to the condition of this study, to measure accurately the $CO_2$ evolution rate. If the $CO_2$ evolution rate is very low ($\leqq 5$ $\mu$L/h), the headspace 17 of the respirometer 11 should be kept minimal to hasten the reaching of the steady-state The respirometer 11 was designed so that the size of the reaction chamber 12 stays the same while the size of the sample vial 13 may vary according to the need of samples and the requirement of a minimal headspace 17.

Figure 5:
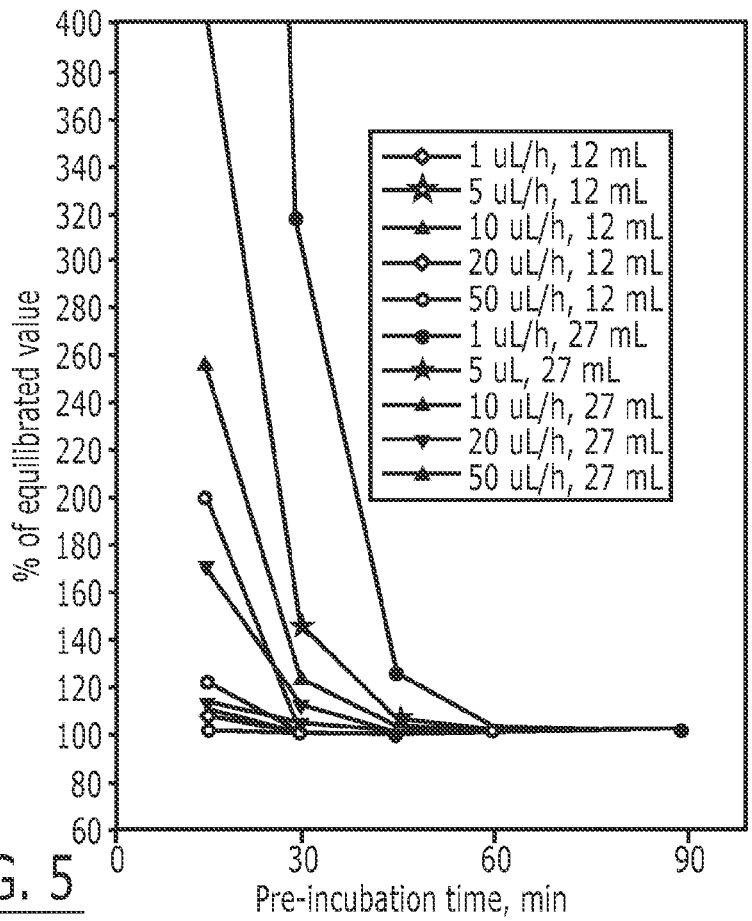
FIG. 5 is a graph of the headspace $CO_2$ concentration, expressed as a percent of the final steady-state headspace $CO_2$ concentration versus time of pre-incubation for a range of respiration rates.
Figure 6:
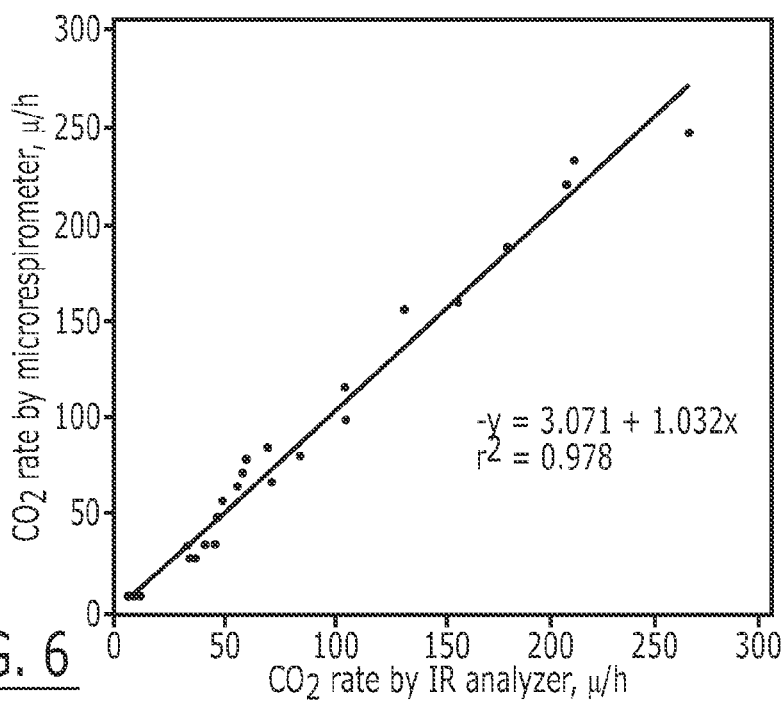
FIG. 6 is a graph of $CO_2$ evolution rate determined by the microrespirometer versus that determined by an infrared analyzer.

A validation experiment was performed by comparing results using the microrespirometer 11 with a method using an ir analyzer such as known in the art (FIG. 5). Portions of soil samples of relatively low $CO_2$ evolution rates (2–5 $\mu$L/h/g), unfrozen processed meat samples of medium $CO_2$ evolution rates (10–100 $\mu$L/h/5 g), and room-temperature milk samples of high $CO_2$ evolution rates (80–280 $\mu$L/h/20 mL) were placed in 25-mL sample vials 13. The $CO_2$ evolved by microorganisms associated with each sample was determined by the microrespirometer 11 method of the present invention. A duplicate sample in another 25-mL sample vial 12 was also placed in a 250-mL flask, and the $CO_2$ evolution rate was determined by the ir analyzer method known in the art. The sample vials 12 in the microrespirometers 11 and those in the 250-mL flasks of the ir analysis method were exchanged, and the $CO_2$ evolution rates determined again with the alternate methods.

One of the advantages of the microrespirometer 11 is its ability to determine the $CO_2$ evolution rate accurately at the $\mu$L/h level in a short time. Determination of the $CO_2$ evolution rates at a $\mu$L/h level is quite a challenge even for a sophisticated ir method. The IR analyzer must be able to detect less than 10 ppm (v/v) changes of $CO_2$ concentration with certainty during a period of hours. The accuracy of an IR analyzer method is further limited by the uncertainty of the volume occupied by a solid sample, and, therefore, that of the headspace, in most cases. Variation of headspace humidity, pressure, and temperature all affect the accuracy and precision of an ir respirometer. Because the microrespirometer method is based on the principle of $CO_2$ absorption-evolution steady state, its accuracy is not affected by headspace volume, humidity, pressure, or initial $CO_2$ concentration. The simplicity, noninstrumental nature, and very modest costs of the microrespirometer 11 make it available to many laboratory and field applications where accurate and rapid determination of respiration rate is desired.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for measuring an evolution rate of carbon dioxide from a sample in µL/h range, the method comprising the steps of:
   pre-incubating the sample in gas communication with a solution comprising a diluted, less than 0.01M, alkaline solution and a pH indicator by shaking the sample and the solution to enhance absorption of carbon dioxide dissolved in the solution;
   permitting the alkaline solution to absorb carbon dioxide formed by the sample in an enclosed space;
   following the pre-incubating step, determining from a change in the pH indicator a time increment at which an increment of the alkaline solution is substantially consumed by the carbon dioxide;
   calculating from the time increment the carbon dioxide evolution rate.

2. The method recited in claim 1, wherein the shaking step comprises shaking at a fixed rate.

3. The method recited in claim 1, wherein the alkaline solution comprises sodium hydroxide and barium chloride.

4. The method recited in claim 1, wherein the indicator comprises phenolphthalein.

5. The method recited in claim 4, wherein the indicator further comprises an ethanol solution.

6. The method recited in claim 1, wherein the pre-incubating step comprises:
   a. placing the sample in gas communication with a first amount of the solution comprising the alkaline solution and the pH indicator, the first amount more than sufficient to absorb carbon dioxide formed during a predetermined amount of time;
   b. permitting the alkaline solution to absorb formed carbon dioxide in the enclosed space for the predetermined amount of time; and
   c. withdrawing at least a portion of the non-consumed alkaline solution to leave a predetermined portion of the non-consumed alkaline solution in the reaction chamber following the step (b).

7. The method recited in claim 6, wherein the withdrawing step comprises withdrawing substantially all of the solution.

8. The method recited in claim 7, wherein step the first amount comprises a predetermined quantity of the alkaline solution.

9. The method recited in claim 1, wherein the pre-incubating step comprises injecting a predetermined quality of the alkaline solution into the reaction chamber.

10. The method recited in claim 9, further comprising the steps of:
    repeating the pre-incubating, permitting, and determining steps a predetermined number of times; and
    averaging the time increments from the repeated pre-incubating, permitting, and determining steps; and wherein
    the calculating step comprises calculating from the averaged time increment the carbon dioxide evolution rate.

11. The method recited in claim 1, wherein the change in the pH indicator comprises a visualizable color change.

12. The method recited in claim 1, wherein the calculating step comprises using the following equation:

$$\text{carbon dioxide evolution rate (µmol/h)} = (V \times 10^3 \times M/2)/(t/60),$$

wherein M is the molarity of the alkaline concentration of the solution, V is a volume of the increment of the alkaline solution in millileters, and t is the time increment in minutes.

* * * * *